United States Patent
Sharma et al.

(10) Patent No.: US 9,541,279 B2
(45) Date of Patent: Jan. 10, 2017

(54) CANDLE DISPENSER

(71) Applicant: S.C. Johnson & Son, Inc., Racine, WI (US)

(72) Inventors: Nitin Sharma, Kenosha, WI (US); Allyce M. Gilligan, Milwaukee, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 345 days.

(21) Appl. No.: 13/920,123

(22) Filed: Jun. 18, 2013

(65) Prior Publication Data
US 2014/0370450 A1    Dec. 18, 2014

(51) Int. Cl.
C11C 5/00     (2006.01)
F21V 35/00    (2006.01)
A01M 1/20     (2006.01)
A61L 9/03     (2006.01)

(52) U.S. Cl.
CPC ............ F21V 35/00 (2013.01); A01M 1/2088 (2013.01); A61L 9/03 (2013.01); C11C 5/006 (2013.01); A61L 2209/133 (2013.01)

(58) Field of Classification Search
CPC .............. C11C 5/00; C11C 5/02; F21V 35/00; A61L 2209/133; A61L 9/03; A01M 1/2088
USPC ............ 431/4, 288–297; 126/263.01, 263.04
See application file for complete search history.

(56) References Cited

U.S. PATENT DOCUMENTS

| | | | | | |
|---|---|---|---|---|---|
| 746,942 | A | * | 12/1903 | Feval | A61L 2/20 422/305 |
| 1,243,439 | A | * | 10/1917 | Myers | A47J 27/10 122/234 |
| RE18,623 | E | * | 10/1932 | Root | F21V 35/00 362/161 |
| 1,920,599 | A | * | 8/1933 | Schuh | A61L 9/03 362/437 |
| 2,714,649 | A | * | 8/1955 | Schum | A01M 1/2083 219/541 |
| 2,742,342 | A | | 4/1956 | Dew et al. | |
| 2,775,006 | A | * | 12/1956 | Kranc | A01M 1/2088 235/144 M |
| 2,813,187 | A | * | 11/1957 | Riba Rovifa | A01M 1/2077 219/385 |

(Continued)

FOREIGN PATENT DOCUMENTS

| | | |
|---|---|---|
| GB | 2059434 A | 4/1981 |
| WO | WO 01/59047 A1 | 8/2001 |
| WO | WO 2007/012036 A1 | 1/2007 |

OTHER PUBLICATIONS

A September 2012 photograph of a Cutter insect repellent lantern, the lantern being admitted prior art.

(Continued)

*Primary Examiner* — Gregory Huson
*Assistant Examiner* — Martha Becton (57) ABSTRACT

Devices dispenser air treatment chemicals in response to heat generated by a candle. Heat transfer elements carry flame heat to an impregnated substrate that is positioned mostly or entirely below the candle. The air treatment chemical vapors are kept away from prolonged direct exposure to flame heat, thereby reducing heat degradation of the active. The candle automatically adjusts heat transfer rates to correct for decreasing amounts of active on the substrate as the substrate sears being used up.

20 Claims, 10 Drawing Sheets

(56) References Cited

U.S. PATENT DOCUMENTS

| | | | | |
|---|---|---|---|---|
| 3,105,373 | A * | 10/1963 | De Villemure | C11C 5/006 431/288 |
| 3,279,118 | A * | 10/1966 | Allen | A01M 1/2088 128/203.12 |
| 3,285,694 | A * | 11/1966 | Marchi | A01M 1/2066 422/305 |
| 3,367,758 | A * | 2/1968 | Ambrose | A01G 13/06 126/59.5 |
| 3,586,473 | A * | 6/1971 | Galloway | C11C 5/004 431/126 |
| 3,797,990 | A * | 3/1974 | Rogers | F21V 35/00 431/288 |
| 4,013,397 | A * | 3/1977 | Neugart | F23D 3/24 431/289 |
| 4,028,045 | A * | 6/1977 | Reiher | C11C 5/008 422/4 |
| 4,449,987 | A * | 5/1984 | Lindauer | C11C 5/002 424/40 |
| 4,693,890 | A * | 9/1987 | Wilson | A01N 25/20 424/DIG. 10 |
| 4,696,676 | A * | 9/1987 | Wilson | A01N 25/20 44/275 |
| 4,748,860 | A * | 6/1988 | Butler | A01N 25/20 424/84 |
| 4,759,228 | A * | 7/1988 | Butler | A01N 25/20 424/84 |
| 4,781,895 | A | 11/1988 | Spector | |
| 4,839,144 | A * | 6/1989 | Martin | A61L 9/03 206/524.3 |
| 4,849,181 | A * | 7/1989 | Kelley | A61L 9/03 239/54 |
| 5,574,821 | A * | 11/1996 | Babasade | 392/392 |
| 5,578,089 | A * | 11/1996 | Elsamaloty | C11C 5/004 431/288 |
| 5,833,971 | A * | 11/1998 | Baldwin | A61L 9/042 424/401 |
| 5,891,400 | A | 4/1999 | Ansari et al. | |
| 5,927,965 | A * | 7/1999 | Pappas | C11C 5/006 264/247 |
| 6,033,212 | A * | 3/2000 | Bonnema | A01M 1/2083 239/139 |
| 6,129,771 | A * | 10/2000 | Ficke et al. | 44/275 |
| 6,309,986 | B1 | 10/2001 | Flashinski et al. | |
| 6,337,080 | B1 | 1/2002 | Fryan et al. | |
| 6,465,645 | B1 * | 10/2002 | Wood | C08K 5/34926 44/275 |
| 6,482,365 | B1 | 11/2002 | Seller | |
| 6,503,459 | B1 * | 1/2003 | Leonard | A01M 1/2088 422/120 |
| 6,780,382 | B2 | 8/2004 | Furner et al. | |
| 6,802,707 | B2 * | 10/2004 | Furner | F23D 3/16 431/292 |
| 7,138,130 | B2 | 11/2006 | Davis et al. | |
| 7,247,017 | B2 * | 7/2007 | Furner | F21V 37/00 431/292 |
| 7,287,978 | B2 | 10/2007 | Kubicek et al. | |
| 7,467,944 | B2 * | 12/2008 | Furner | 431/289 |
| 7,467,945 | B2 * | 12/2008 | Kubicek | F23D 3/16 431/289 |
| 7,497,685 | B2 * | 3/2009 | Kubicek | C11C 5/006 362/161 |
| 7,524,187 | B2 * | 4/2009 | Kubicek | F23D 3/16 431/289 |
| 7,607,915 | B2 * | 10/2009 | Adair | A61L 9/037 431/289 |
| 7,629,001 | B2 | 12/2009 | Davis et al. | |
| 8,047,837 | B2 | 11/2011 | Furner et al. | |
| 8,439,669 | B2 * | 5/2013 | Masterson | A01M 1/2088 239/135 |
| 2002/0102187 | A1 * | 8/2002 | Bellenger | A61L 9/035 422/126 |
| 2004/0175287 | A1 * | 9/2004 | Nakatsu | A61L 9/035 422/4 |
| 2005/0019238 | A1 * | 1/2005 | Hart | A01M 1/2066 422/306 |
| 2005/0037306 | A1 * | 2/2005 | Nakatsu | C11C 5/008 431/291 |
| 2005/0150154 | A1 * | 7/2005 | Maat | C11C 5/008 44/275 |
| 2006/0057524 | A1 | 3/2006 | Jameson | |
| 2006/0057528 | A1 * | 3/2006 | Kubicek | 431/292 |
| 2006/0057529 | A1 * | 3/2006 | Kubicek | F23D 3/16 431/325 |
| 2006/0057530 | A1 * | 3/2006 | Kubicek | F23D 3/16 431/325 |
| 2006/0084021 | A1 * | 4/2006 | Kubicek | F23D 3/24 431/291 |
| 2007/0026352 | A1 * | 2/2007 | Kubicek | F23D 3/24 431/289 |
| 2007/0183932 | A1 * | 8/2007 | Adair et al. | 422/88 |
| 2007/0292812 | A1 | 12/2007 | Furner et al. | |
| 2007/0292813 | A1 * | 12/2007 | Adair | C11C 5/002 431/291 |
| 2009/0004067 | A1 | 1/2009 | Furner et al. | |
| 2009/0293341 | A1 * | 12/2009 | Fleming | A01M 1/04 43/113 |
| 2009/0294553 | A1 * | 12/2009 | Wang | A01M 29/12 239/135 |
| 2010/0053935 | A1 * | 3/2010 | Shen | A01M 29/12 362/96 |
| 2010/0270391 | A1 * | 10/2010 | Allison | A01M 1/2088 239/44 |
| 2013/0101946 | A1 * | 4/2013 | Masterson | F23D 3/18 431/292 |
| 2014/0199646 | A1 * | 7/2014 | Beadles | C11C 5/002 431/288 |
| 2014/0252263 | A1 * | 9/2014 | Besselievre | E04B 1/80 252/62 |

OTHER PUBLICATIONS

PCT/US2014/041924 International Search Report and Written Opinion dated Jan. 5, 2015.

* cited by examiner

CANDLE DISPENSER

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to devices that dispense air treatment chemicals from a substrate using the heat of a candle to drive the dispensing. More particularly, the invention relates to such devices that have been configured to protect the air treatment chemical from heat degradation (a/k/a "pyrolysis") during such dispensing.

A variety of devices are known for dispensing volatilizable air treatment chemicals such as pest control materials (e.g., insecticides, insect repellents, or insect growth control regulators), air scents or deodorizers (e.g. masks), allergen control ingredients, disinfectants, sanitizers or other materials. In some of these devices the air treatment chemical is mixed with candle wax and is dispensed during a candle burning process (where the chemical is released primarily from the heated wax surrounding the wick). While this is a common technique for dispensing a variety of fragrances, typically it has been less successful when dispensing certain particularly desirable pest control materials.

Attempts have been made to use the heat from a candle (or other similar heat source) to distribute air treatment chemicals from an adjacent impregnated pad surface or the like. See e.g. U.S. Pat. Nos. 2,742,342, 4,781,895, 6,482,365, 6,503,459, and 7,138,130. However, these devices typically placed the pad directly over the candle flame, leading to heat spikes directly ever the flame, as wed as sometimes too little heat adjacent the periphery of the pad.

Another approach was to position a chimney directly over the candle flame, with the impregnated substrate positioned around the chimney. See e.g., U.S. Pat. No. 8,047,837. While this made the pad able to more efficiently dispense some additional types of air treatment chemicals, it did not completely address pyrolysis and/or uneven healing problems.

Still another approach was disclosed in U.S. patent application publication 2009/0004067. There, an air treatment chemical was coated on a radially outer periphery of a candle cap. The heat of the candle heated the walls of the candle cup, and that heat was used to drive the air treatment chemical off. However, this type of heat transfer was relatively inefficient, and (in any event) placing the active at a typical gripping position for the candle could cause some consumers to have concerns about the possibility of touching and/or interfering with the active.

Thus, a need continues to exist for improved candle dispensers where the heat of a candle drives an air treatment chemical off of a carrier substrate, albeit with reduced pyrolysis concerns.

BRIEF SUMMARY OF THE INVENTION

In one aspect the invention provides a device for dispensing an air treatment chemical. The device has a housing for supporting a candle and a candle supported on that housing. The candle has a wick that can be lit to create a flame fueled by the candle. There is also a substrate bearing an air treatment chemical positioned at least in part under the candle.

In preferred forms a heat transfer fin is positioned adjacent the candle wick, the heat transfer fin comprises a metal such as aluminum, and the heat transfer fin widens in a downward direction such that as more of the candle is used up more of the fin can be directly exposed to heat generated from a flame of the candle. The heat transfer fin transfers heat from the candle flame to a heat transfer radial extension that extends under the candle.

The substrate is preferably positioned under the heat transfer radial extension such that heat from a candle flame can be used to drive air treatment chemical off of the substrate. In one form the substrate comprises sand coated with a binder, and the housing has a support ledge for supporting the candle and has an inlet for providing air to the candle.

In another aspect the invention provides a device for dispensing an air treatment chemical. It has a housing for supporting a candle, a candle supported on the housing, the candle having a wick that can be lit to create a flame, and a substrate bearing an air treatment chemical that is mounted at least in part under the candle. The substrate is positioned such that heat from the candle flame, if the wick is lit, can drive air treatment chemical out of the housing (e.g. out of a radial outlet, or past the flame area out of the housing via an axial side channel).

In still other forms of the invention there is provided a refill for a device of the above kind. The refill has a container, candle wax in the container, a wick extending in the candle wax, and a heat transfer structure mounted below and also axially along the candle wax. The heat transfer structure comprises an axially extending fin structure and a lower radial extension, the fin structure being positioned at least in part adjacent an upper portion of the wick. There is also a porous substrate positioned adjacent the radial extension, the porous substrate bearing the air treatment chemical if the wick is lit, heat from a flame created thereby can heat the fin structure, which can transfer heat to the lower radial extension, which can transfer heat to the porous substrate, which can then dispense air treatment chemical.

It is particularly preferred that the fin structure widen in a downward direction, and there can be a peel off cover positioned under a lower side of the substrate until just before use. The heat transfer structure can be made of aluminum, and the refill can, for example have at least 10 gm of wax and at least 10 mg of air treatment chemical.

Some embodiment of the invention provide lower radial outlet(s) below the candle that direct air treatment chemical away from flame vapors. Other embodiments cause air treatment chemical to pass up an axial side channel past the flame area and then out of the housing. Regardless, the invention helps avoid exposing most of the active to prolonged periods of direct flame heat.

Heat from burning of the candle passes to the substrate so drive air treatment chemical off the substrate (and ultimately out of the housing). Placing the substrate below the candle allows candle wax to insulate heat spikes adjacent the substrate. Because less direct heat is reaching the substrate than if the substrate were directly over the flame, the substrate is preferably altered to more easily release active upon heating. This can be achieved in a number of ways, most preferably by forming the substrate of a sand core mixed with a binder resin, and/or by using a very volatile active.

In a preferred form only a single refill unit is required to use the assembly (as distinguished from requiring a separate wax refill and a separate substrate refill). This makes the device more intuitive for consumers to use (e.g., detailed use instructions are not required). The consumer merely places a refill on a platform, and lights the candle as they would for a standard candle.

In the most preferred embodiments the system self-adjusts as the substrate gets closer and closer to being "used up". As that is about to happen (as the amount of candle wax decreases), the heat reaching the substrate will increase, thereby insuring that the rate of dispensing does not drop off sharply too quickly.

Certain embodiments of the invention also help prevent unintended human contact with the substrate since the substrate is neither directly above the candle flame, nor accessible on a radial periphery of the housing. Moreover, the components of the assembly are relatively inexpensive to produce.

The foregoing and other advantages of the present invention will be apparent from the following description of the preferred embodiments. As these embodiments are merely illustrative, they are not intended to represent the full scope of the invention. Thus, reference should therefore be made to the claims herein for interpreting the scope of the invention.

DETAILED DESCRIPTION OF THE PREFERRED EMBODIMENTS

Figures 4, 5:
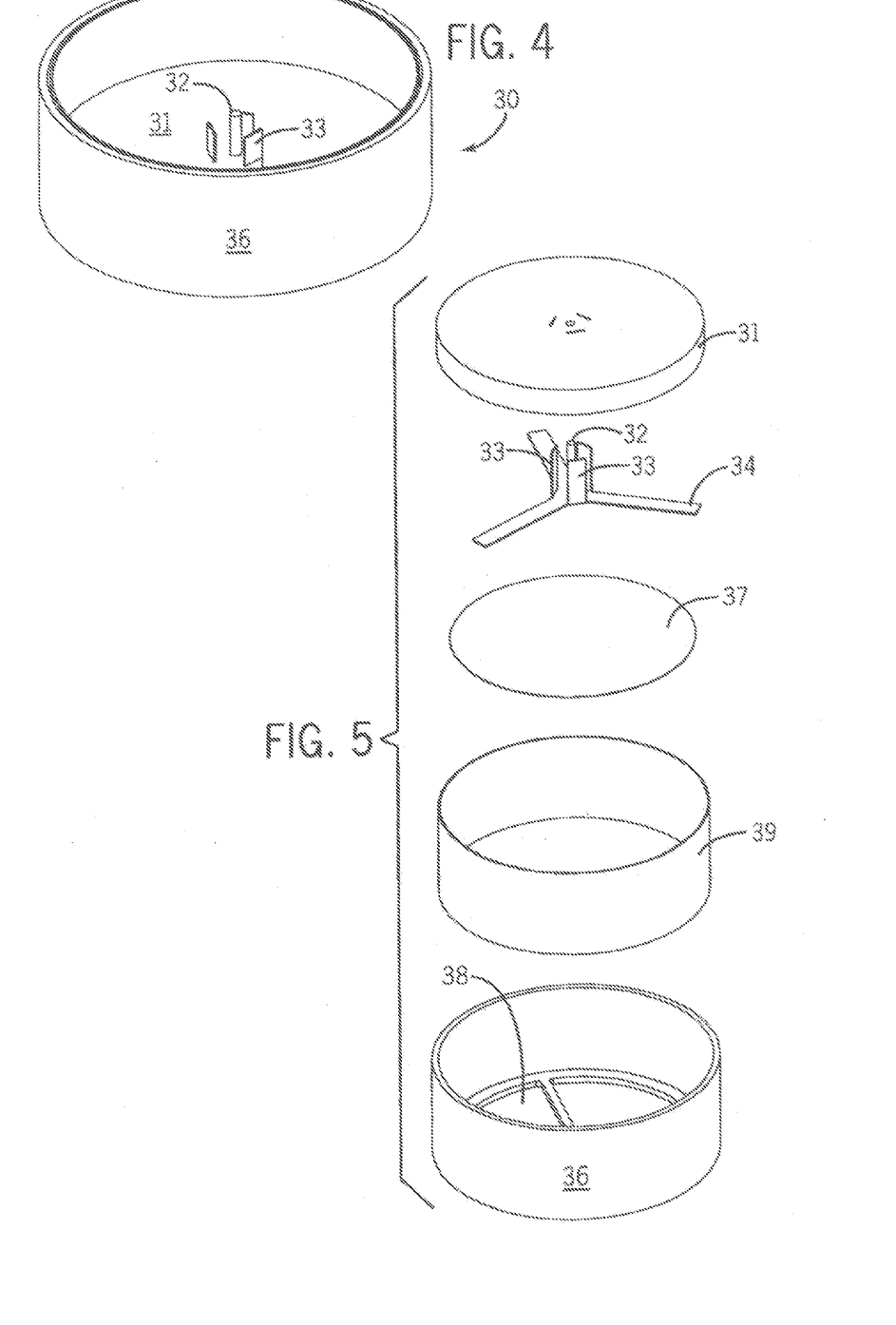
FIG. 4 is a perspective view of a candle refill structure of FIG. 1, albeit shown separated from the outer housing of FIG. 2.
FIG. 5 is an exploded perspective view of the candle refill structure of FIG. 4.

A first assembly 9 for dispensing an air treatment chemical is shown in FIGS. 1-5. Its major subcomponents are an outer housing 10 (FIG. 2) and a candle/substrate refill 30 (FIG. 4).

Figure 1:
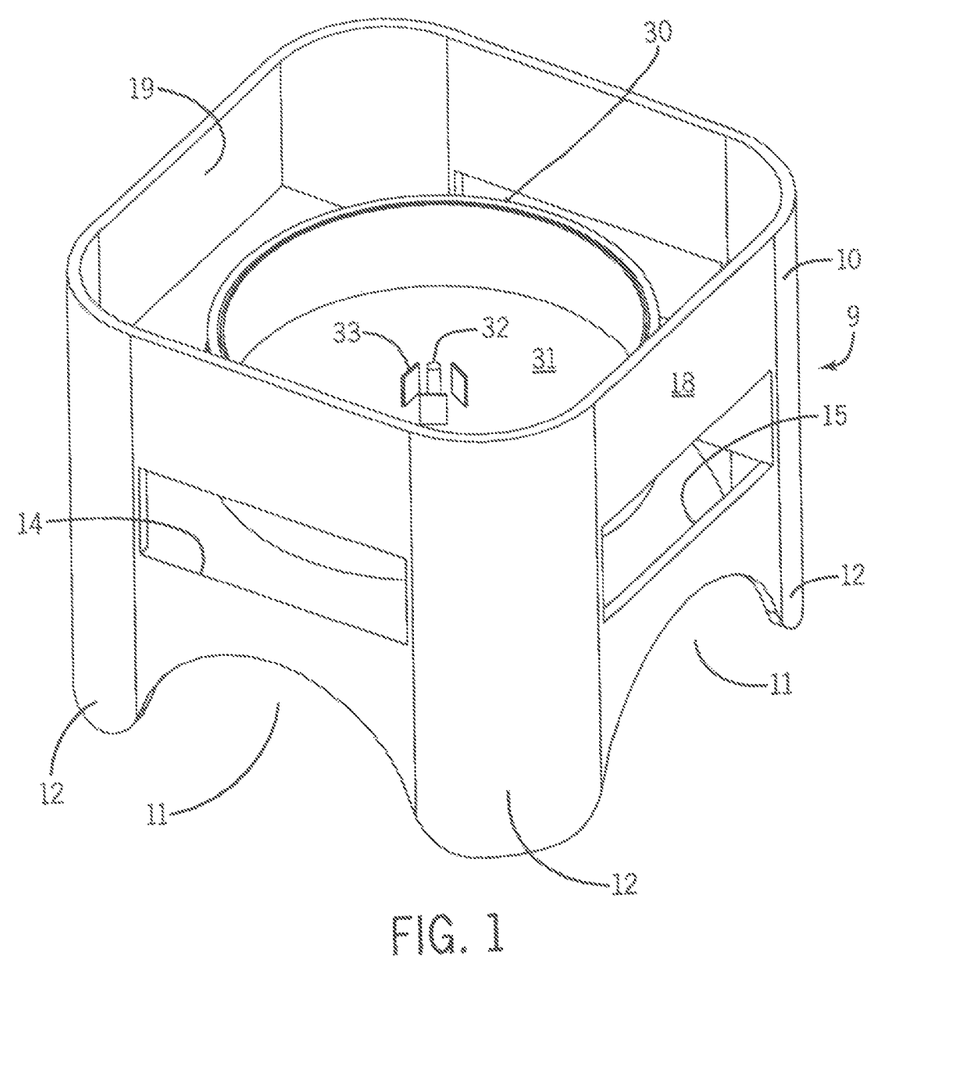
FIG. 1 is an upper perspective view of a first candle dispenser embodiment of the present invention.
Figure 2:
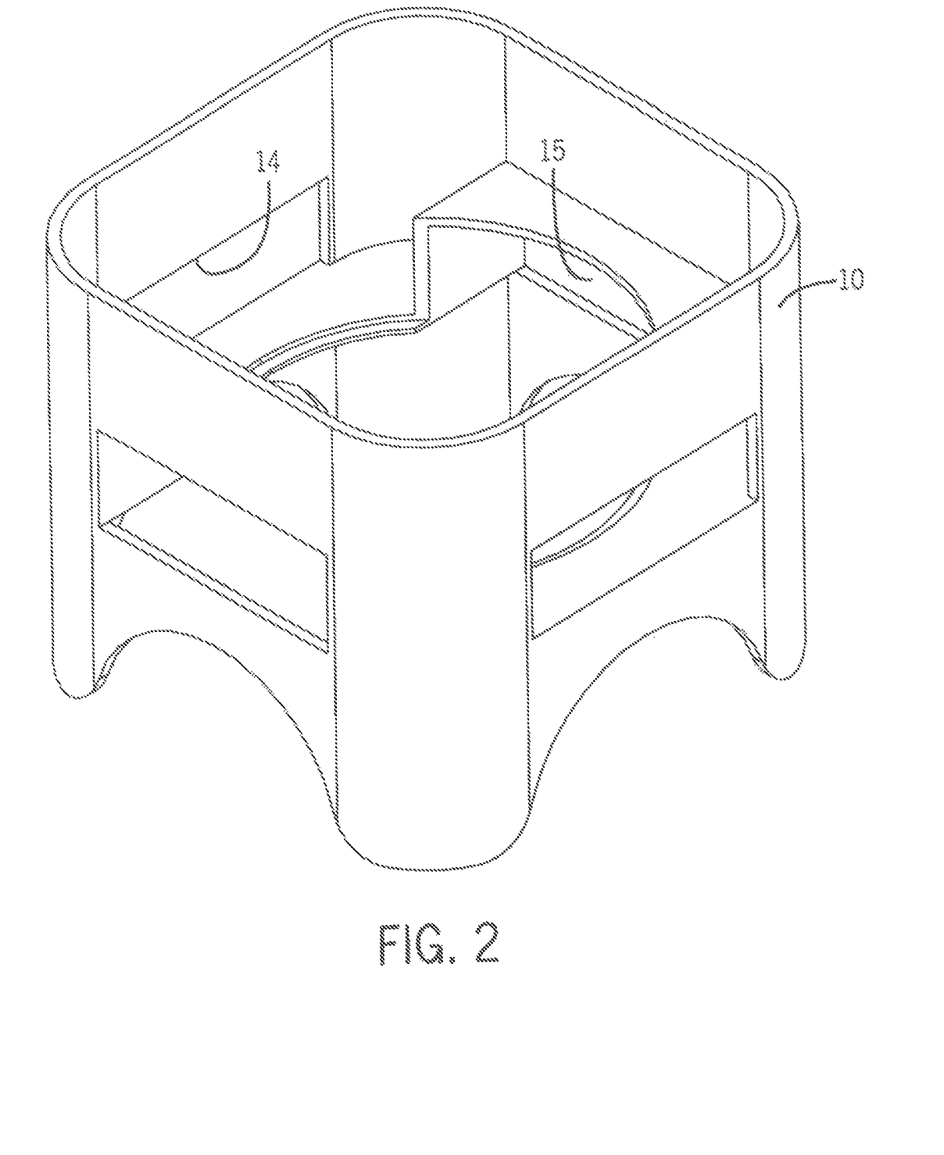
FIG. 2 is a treated upper perspective view of an outer housing portion thereof.
Figure 3:
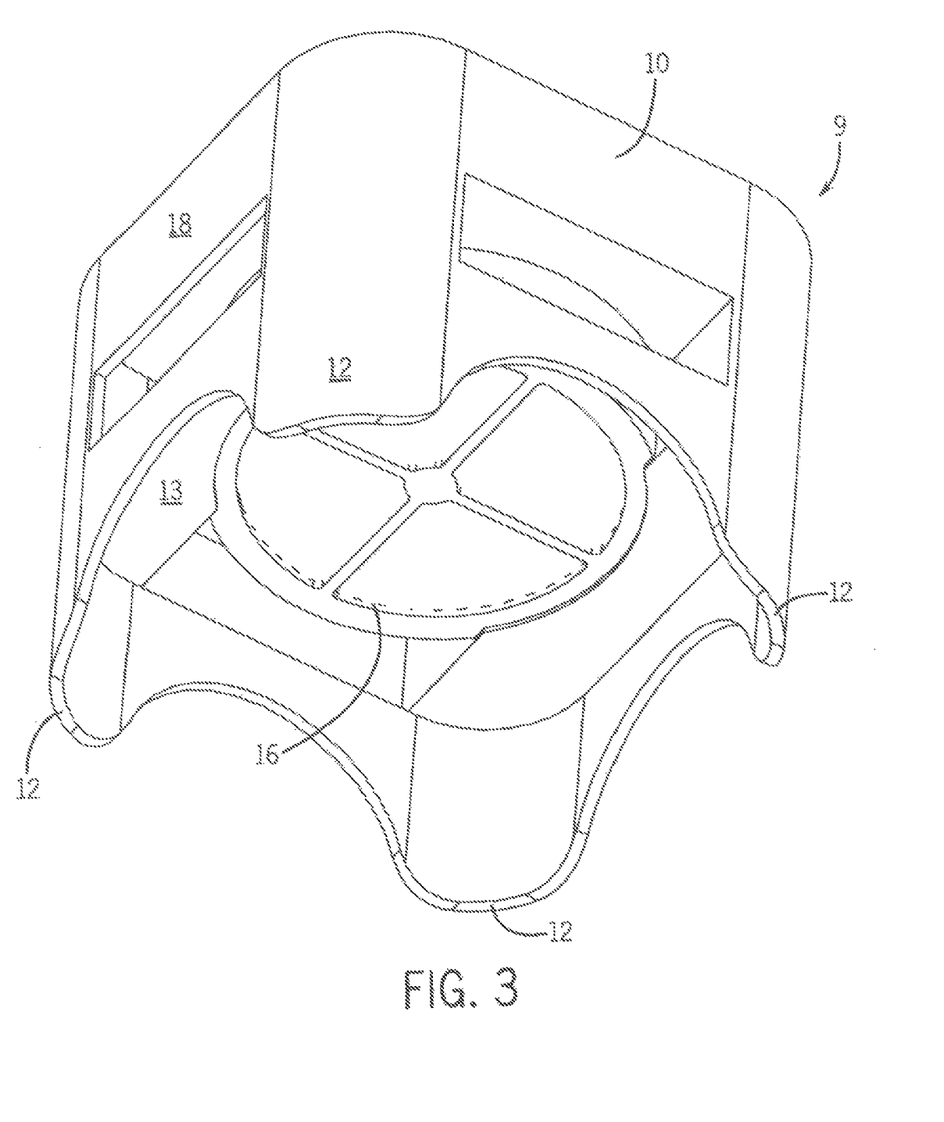
FIG. 3 is lower perspective view of the FIG. 1 assembly.

The outer housing 10 is in the form of a four-legged lower table that has arched apertures 11 between corner legs 12. A base portion or support/platform 13 extends horizontally adjacent a first set of opposed slit openings 14, and a second set of opposed slit openings 15. The support/platform 13 has a central, circular opening 16. Upper walls 18 define an internal cavity 19 for holding the refill 30.

Refill 30 is sized so as to fit within the internal cavity 19, with a bottom portion of the refill open to the area defined by the legs 12 under opening 16. Enough space is left in the internal cavity 19 around the refill 30 so that air may easily pass into opposed slit openings 15, up outside the refill 30, and to the area of the candle wick. This helps feed fresh air to the candle, and ultimately helps carry flame vapors out of the outer housing 10.

The refill 30 has a sleeve-like container 36 in which is positioned a wax disk 31 through which extends a wick 32. Adjacent the wick in the wax are positioned multiple axially extending heat transfer fins 33 that may be made of a metal such as aluminum or steel, and which are preferably integrated into a lower metal "spider" having radial extensions 34. Heat from a candle flame can be carried by a heat transfer structure down to and then along these extensions, and then passed to disk form substrate 37. Optionally, an insulating sleeve 39 may be positioned in the container 36.

While the substrate may be made of various porous materials, in one preferred form it is made of silica sand coated with a binder such as novolac resin. See generally U.S. Pat. No. 7,629,001. This is then impregnated with an air treatment chemical such as a repellent that has been dissolved in a hydrocarbon solvent. When a peel-off seal (compare peel-off seal 40C in FIG. 12) has been removed from the refill 30 (immediately prior to the refill being placed in the outer housing 10), heating of the substrate permits active to be driven downward through aperture 38, opening 16 and then slit openings 14. This pathway directs the dispensed air treatment chemical away from the candle flame vapors. Surprisingly, enough heat still reaches the substrate for effective insect (e.g. mosquito) control.

As the wax is being used up the amount of remaining active on the substrate will decrease. Absent other structures of the present invention this could have reduced the rate of active being dispensed to unacceptably low levels too early in the product life. Thus, it is proposed to widen the fins in the downward direction. As the wax level drops due to the burning of the candle, this increases the amount of fin area exposed to air and then more heat is able to reach the fin area. This increases the amount of heat reaching the substrate, and thereby helps keep the dispensing rate more constant, for longer.

Figure 6:
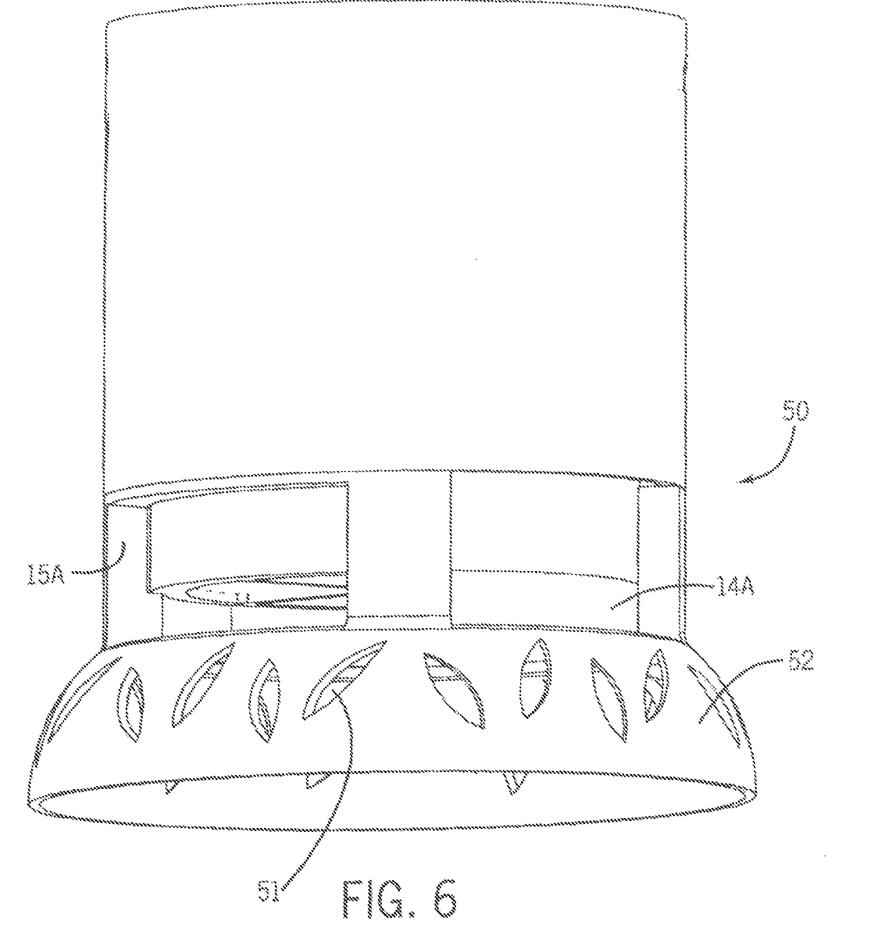
FIG. 6 is a perspective view of an alternative embodiment of a candle dispenser.

Light projected by the candle provides an additional light source, as well as desired aesthetics (e.g. when ornamental apertures like radial holes 51 are used, or upper walls 18 are transparent). This is notwithstanding the desirability of minimizing accidental snuffing of the candle.

The wax disk 31 can be made of a conventional candle wax (e.g. paraffin). Optionally, another secondary air treatment chemical (e.g. a fragrance, citronella) may be mixed in with the wax. The outer housing 10 may alternatively be made of any desired heat resistant material (e.g. a tin plated steel).

Air treatment chemicals may be presented in a wide variety of formulations. See U.S. Pat. Nos. 6,309,986 and 6,337,080 for disclosure of a variety of insect control materials, deodorizers, fragrances, sanitizers, and disinfectants known to be suitable for use with heating dispensers. For example, suitable active materials may include (when the volatile material is an insecticide and/or insect repellent), organic phosphorous insecticides, lipidamide insecticides, natural repellents as citronella oil, natural pyrethrins and pyrethrum extract, and synthetic pyrethroids. Suitable alternative synthetic pyrethroids are acrinathrin, allethrin as D-allethrin, Pynamin, benfluthrin, bifenthrin, biollethrin as Pynamin Forte, S-bioallethrin, esbiothrin, esbiol, bisoresmethrin, cycloprothrin, cyhalothrin, lambda-cyhalothrin, cyphenothrin, empenthrin, esfenvalerate, fenpropathrin, fenvalerate, flucythrinate, taufluvalinate, kadethrin, metoflufenthrin, phenothrin, prallethrin as Etoc, resmethrin, tefluthrin, tetramethrin, or transfluthrin. It is preferred to use a more volatile active when seeking insect control in a large space or outdoors on a patio. For example, one can use metoflufenthrin or transfluthrin where mosquito control is of primary interest.

When the active is applied to the substrate it may be coated on or impregnated in various ways. For example, the active can be mixed into a hydrocarbon or other solvent, and drops of the mix can be released above the substrate.

The amount of candle wax can be coordinated with the characteristics of the substrate and air treatment chemical such that just as the candle wax is being used up the air treatment chemical is being used up as well. Alternatively, there can be a color change cue or other timing feature associated with the wax which advises the public as to an optimal time to replace the refill.

The refill 30 is intended to be sold in packaging designed to inhibit release of active before use (beyond what the peel off seal achieves). For example, there can be a tear open pouch (not shown) in which the refill is positioned prior to use.

While the above describes a first embodiment of the present invention, it should be appreciated that other embodiments are also within the intended scope of the invention. For example, the support need not have exactly the same number of openings as shown, and the top of the refill need not be completely within an upper cavity of the outer housing 10.

As shown in FIG. 6, the concept can be implemented with a generally cylindrical structure 50 (see openings 14A and inlet 15A). Note that in this embodiment the air inlets below the substrate of that embodiment do not extend through "legs". Rather, they are radial holes 51 in a skirt 52.

Figure 7:
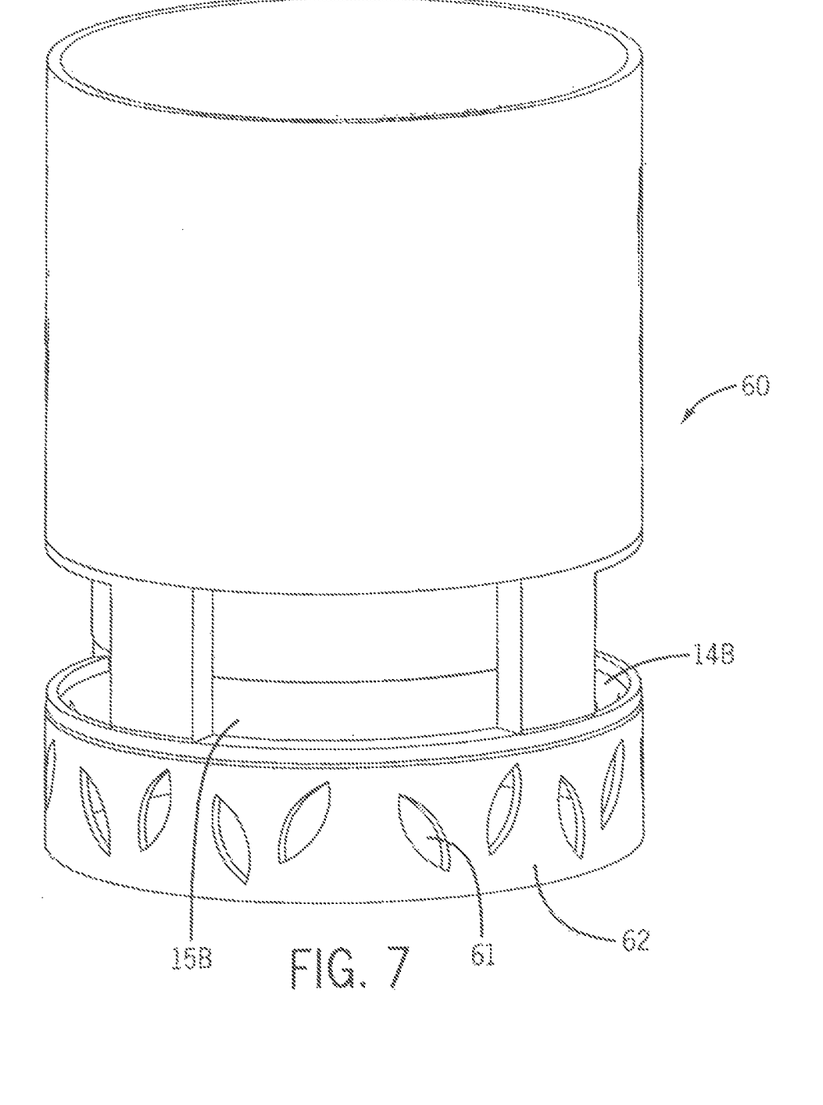
FIG. 7 is another perspective view, but of a third embodiment of a candle dispenser.

A third embodiment (FIG. 7) shows an even more cylindrical structure 60 (having openings 14B and 15B) with a lower skirt 62 having inlets 61.

In the fourth embodiment (FIGS. 8-13) the parts are mostly analogous except that structures are provided to insure that air into which active has been dispensed passes upward, rather than radially outward. Hence, similar or analogous parts have been provided a similar number designation, albeit with a "C" thereafter.

Figure 8:
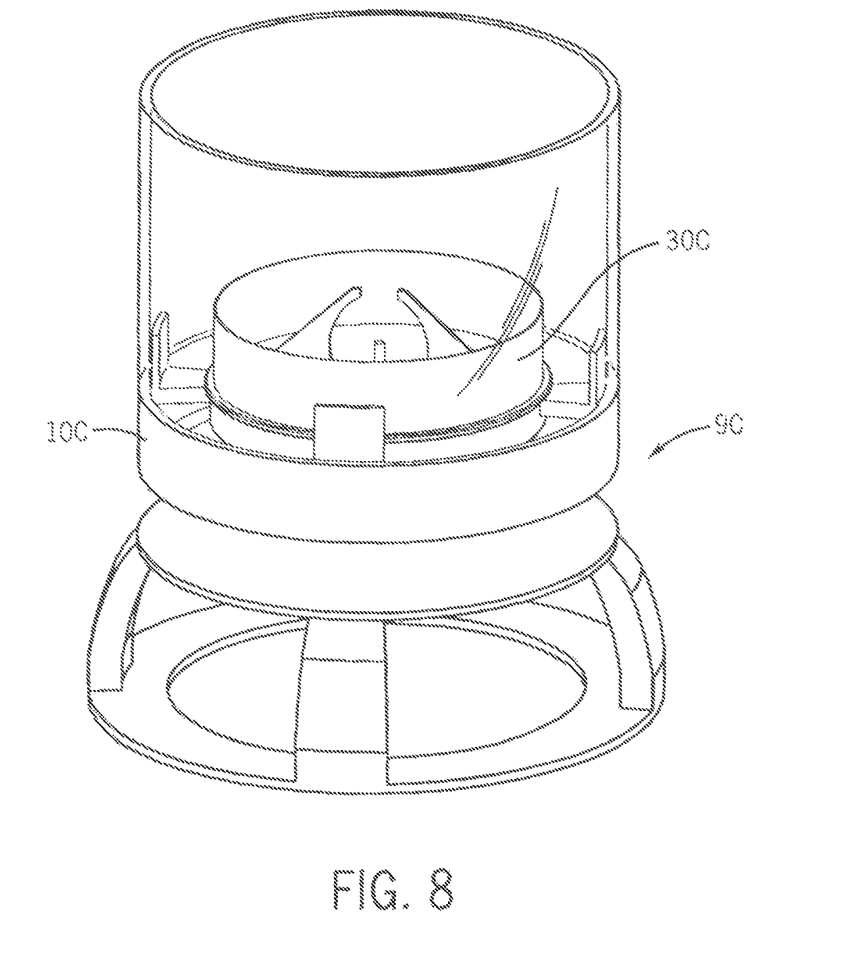
FIG. 8 is a perspective view of a fourth, most preferred, embodiment.

The FIG. 8 assembly 9C has an outer housing 10C in the form of an apertured platform. There is also a refill 30C.

Figure 9:
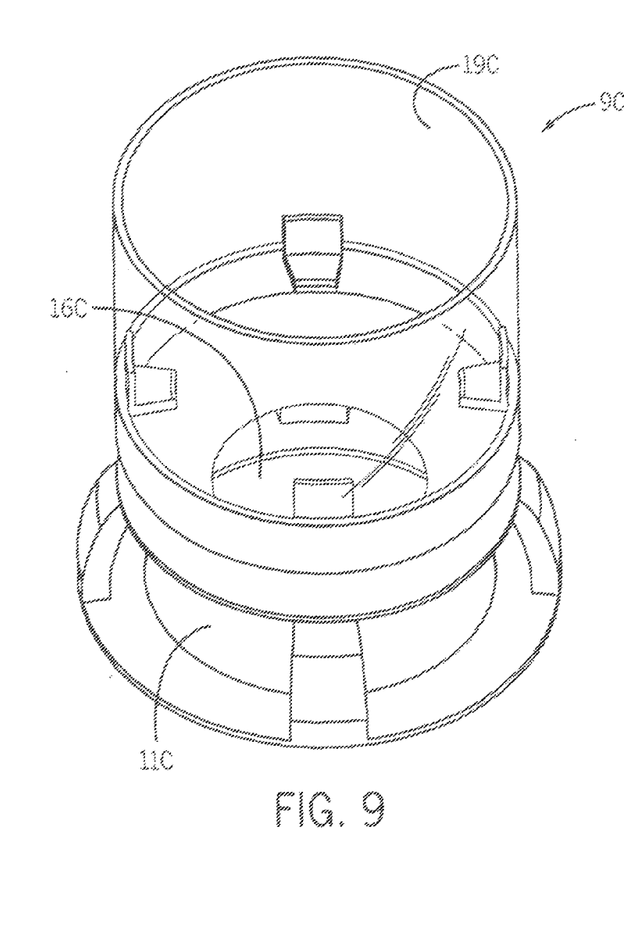
FIG. 9 is another perspective view of the fourth embodiment, but with the candle refill removed.
Figure 10:
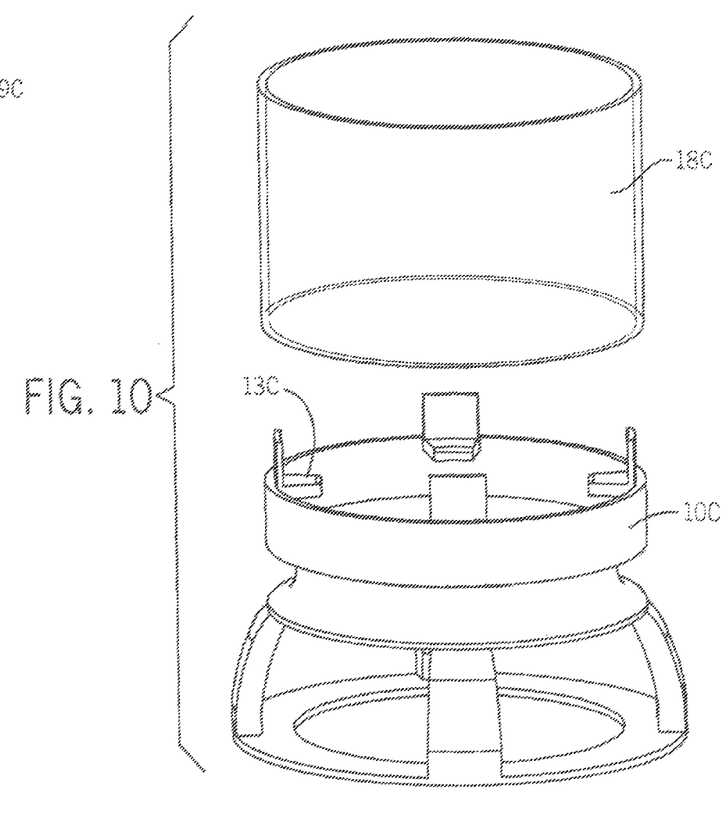
FIG. 10 is an exploded perspective view of the FIG. 9 assembly.
Figure 11:
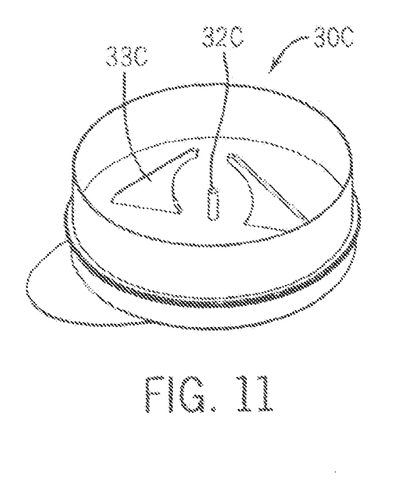
FIG. 11 is a perspective view of a candle refill of the FIG. 8 embodiment.

The lower portion of the outer housing 10C has apertures 11C which allow air to pass in and up through an aperture 16C. Supports/platforms 13C hold the refill 30C away from blocking aperture 16C and the refill has a small enough diameter to permit air to pass up by it inside upper walls 18C (thereby forming an axial side air pathway that is largely distinct from the area of the candle flame) when the refill 30C is placed inside internal cavity 19C.

Figure 12:
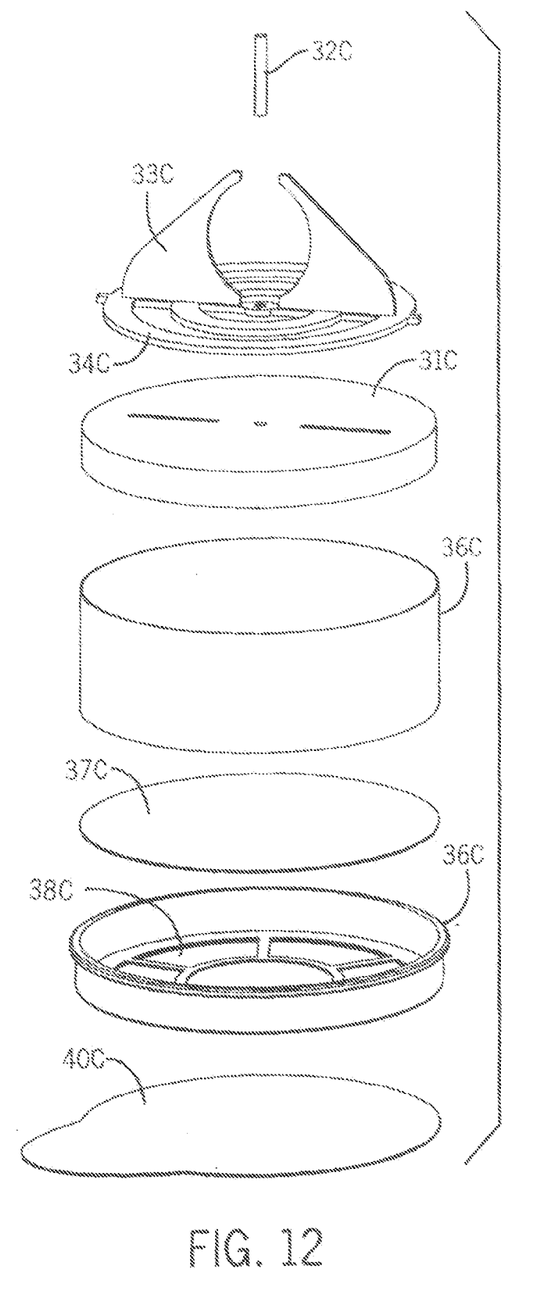
FIG. 12 is an exploded perspective view of the FIG. 11 assembly.

As best understood from FIG. 12, the refill 30C comprises a wax disk 31C having a wick 32C and a heat transfer member 33C/34C. The heat transfer member has fins 33C that extend through the wax disk 31C to carry heat from the flame area down to a radially extending portion 34C. These parts are inserted into container 36C above an impregnated substrate 37C. Heating of the impregnated substrate 37C permits active to be driven through aperture 38C. A peel-off seal 40C removably covers the bottom of container 36C until use.

Figure 13:
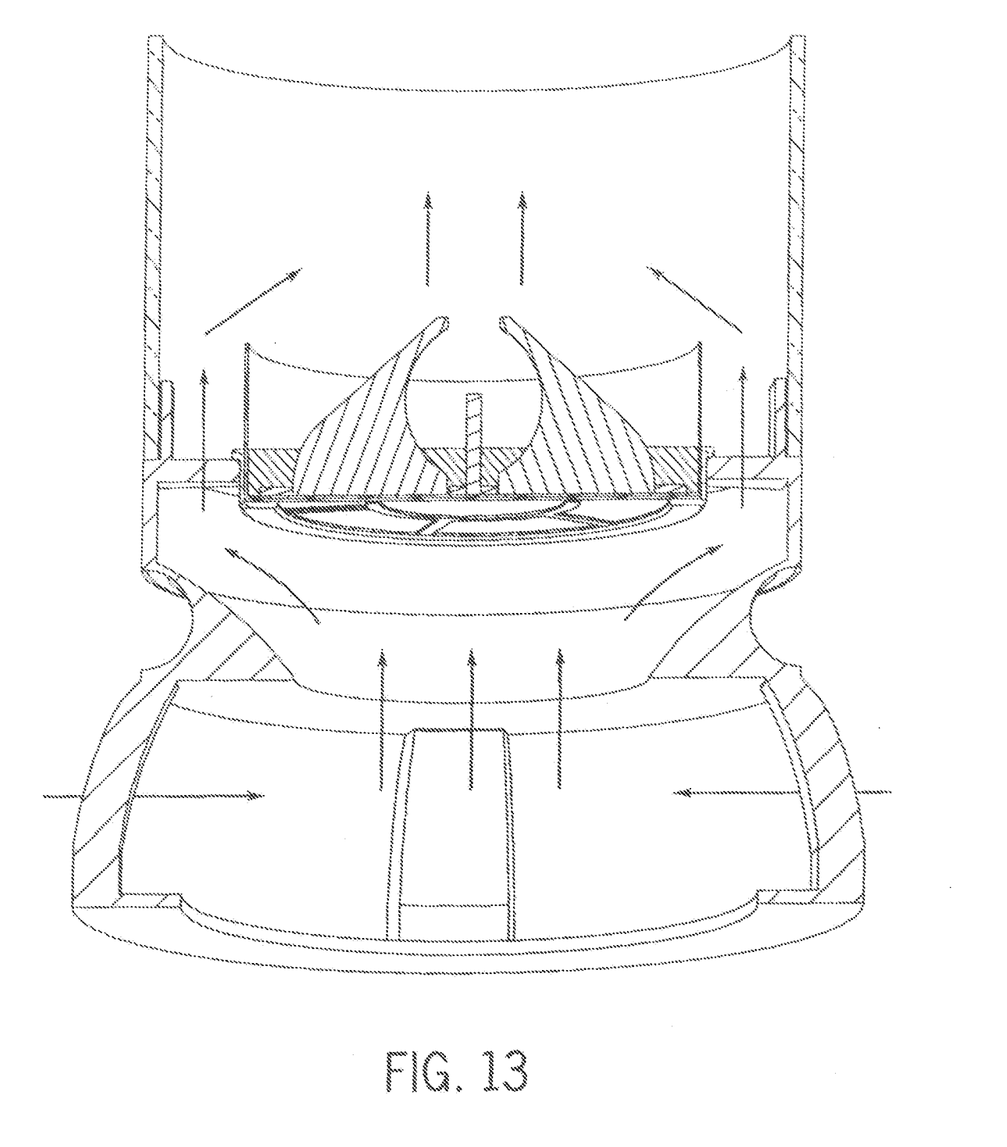
FIG. 13 is a schematic sectional view of the FIG. 8 embodiment, showing the air flow paths.

As will be appreciated from FIG. 13, when using this embodiment air enters through apertures 11C and passes up to the bottom of the refill 30C. Active driven off the substrate 37C mixes into that air and the mix then passes outward and then up between the refill 30C and the wall 18C.

Most of the active laden air is quickly moved past the area of the wick 32C. Thus, even though in this embodiment the active does not radially exit the container below the candle, there is still a substantial reduction in pyrolysis as compared to having the substrate positioned over the candle flame.

As is evident from radially extending portion 34C in FIG. 12, the radial heat transfer extensions can be in other forms then as shown in FIG. 5 at 34. They could also be a simple aluminum disk, or have other radially extending constructions.

Thus, the invention is not to be limited to just the specific embodiments shown or described, and the following claims should be looked to in order to judge the full scope of the invention.

INDUSTRIAL APPLICABILITY

Disclosed herein are improved candle dispenser devices, and refills for use therewith, particularly those designed to reduce unwanted pyrolysis of air treatment chemicals that are dispensed by devices of this general type.

All documents cited in tins patent are, in relevant part, incorporated herein by reference. The citation of any document is not to be construed as an admission that it is prior art with respect to the present invention.

What is claimed is:

1. A device for dispensing an air treatment chemical, the device comprising:
    a housing that supports a container having one or more first apertures, the housing including:
        one or more walls having one or more openings therethrough and defining a cavity, wherein the one or more openings allow air to flow into and out of the cavity; and
        a base portion having at least one second aperture to allow air to enter the cavity;
    candle wax supported by the container, the candle wax supporting a wick that can be lit to create a flame;
    a substrate bearing an air treatment chemical that is mounted at least in part under the candle wax; and
    a heat transfer structure positioned adjacent the wick and extending downward to the substrate,
    wherein, when the wick is lit, the air treatment chemical is driven downward through the one or more first apertures of the container and out of the housing through the one or more openings.

2. The device of claim 1, wherein the heat transfer structure comprises aluminum.

3. The device of claim 1, wherein the heat transfer structure is a fin that widens in a downward direction such that as more of the candle is used up more of the fin can be directly exposed to heat generated from a flame of the candle.

4. The device of claim 3, wherein the heat transfer fin can transfer heat from the candle flame to a heat transfer radial extension that extends under the candle.

5. The device of claim 4, wherein the substrate is positioned under the heat transfer radial extension such that heat from a candle flame can drive air treatment chemical out of the housing.

6. The device of claim 1, wherein the substrate comprises sand coated with a binder.

7. The device of claim 1, wherein the housing has a support ledge for supporting the container.

8. The device of claim 1, wherein the air treatment chemical is selected from the group consisting of insecticides and insect repellents.

9. A device for dispensing an air treatment chemical, the device comprising:
   a housing including:
      one or more walls defining a cavity; and
      a lower skirt having one or more air inlets therethrough to allow air to enter the cavity;
   a container having at least one aperture and being supported within the cavity;
   candle wax supported by the container, the candle wax supporting a wick that can be lit to create a flame;
   a substrate bearing an air treatment chemical that is mounted at least in part under the candle wax; and
   a heat transfer structure positioned adjacent the wick and extending downward to the substrate,
   wherein the substrate is positioned such that heat from the candle flame, if the wick is lit, can drive air treatment chemical through the at least one aperture of the container, into the cavity, and out of the housing.

10. The device of claim 9, wherein the air treatment chemical is selected from the group consisting of insecticides and insect repellents.

11. A refill for a device for dispensing an air treatment chemical, the refill comprising:
   a container having a plurality of apertures;
   candle wax in the container and a wick extending in the candle wax;
   a heat transfer structure mounted at least partially below the candle wax, the heat transfer structure having an axially extending fin structure and a lower radial extension, the fin structure being positioned at least in part adjacent an upper portion of the wick; and
   a porous substrate positioned below and in contact with the radial extension, the porous substrate bearing the air treatment chemical,
   wherein, if the wick is lit, heat from a flame created thereby can heat the fin structure, which can heat the lower radial extension, which can heat the porous substrate, which can then dispense air treatment chemical downward, through at least one of the plurality of apertures.

12. The refill of claim 11, wherein the fin structure widens in a downward direction.

13. The refill of claim 11, further comprising a peel off cover positioned under a lower side of the substrate.

14. The refill of claim 11, wherein, the heat transfer structure comprises aluminum.

15. The refill of claim 11, wherein the refill also comprises at least 10 gm of wax and at least 10 mg of air treatment chemical.

16. The refill of claim 11, wherein the air treatment chemical is selected from the group consisting of insecticides and insect repellents.

17. A refill for a device for dispensing an air treatment chemical, the refill comprising:
   a container having two or more apertures;
   an insulating sleeve positioned within the container;
   candle wax in the container and a wick extending in the candle wax;
   a heat transfer structure mounted to the candle wax; and
   a porous substrate bearing the air treatment chemical positioned at least in part below the candle wax and in contact with the heat transfer structure,
   wherein, if the wick is lit, heat from a flame created thereby can heat the heat transfer structure, which can heat the porous substrate below the candle wax, which can then dispense air treatment chemical downward, through at least one of the two or more apertures.

18. The refill of claim 17, wherein the air treatment chemical is selected from the group consisting of insecticides and insect repellents.

19. The refill of claim 9 further comprising an insulating sleeve positioned within the container.

20. The device of claim 9, wherein the heat transfer structure includes an axially extending fin structure and a lower radial extension.

* * * * *